United States Patent [19]

Erickson

[11] 4,147,694

[45] Apr. 3, 1979

[54] 8-(1H-TETRAZOL-5-YL-CARBAMOYL)-QUINOLINE COMPOUNDS

[75] Inventor: Edward H. Erickson, Woodbury, Minn.

[73] Assignee: Riker Laboratories, Inc., Northridge, Calif.

[21] Appl. No.: 860,625

[22] Filed: Dec. 14, 1977

Related U.S. Application Data

[63] Continuation-in-part of Ser. No. 766,511, Feb. 7, 1977, abandoned.

[51] Int. Cl.$^2$ ............................................. C07D 215/24
[52] U.S. Cl. ............................... 546/169; 424/258; 546/155; 546/157; 546/153
[58] Field of Search ............................ 260/287 F

[56] References Cited

U.S. PATENT DOCUMENTS 3,932,416  1/1976  Bays et al. ................... 260/287 F

FOREIGN PATENT DOCUMENTS 83774    9/1974  Denmark.
2437297  8/1974  Fed. Rep. of Germany.
9249     1973    United Kingdom.

OTHER PUBLICATIONS

Juby, P. F., T. W. Hudyma & M. Brown, "Antiinflammatory 5-(2-Anilinophenyl)tetrazoles, "J. of Med. Chem., vol. 11, pp. 111–117 (1968).
Juby, P. F. & T. W. Hudyma, "J. Med. Chem.," vol. 12, pp. 396–401 (1969).
Burger, A. et al., "Medicinal Chemistry," Interscience Publishers, N.Y., 1960, p. 497.

*Primary Examiner*—Nicholas S. Rizzo
*Assistant Examiner*—Lisa Jones
*Attorney, Agent, or Firm*—Cruzan Alexander; Donald M. Sell; Donald C. Gipple

[57] ABSTRACT

8-(1H-Tetrazol-5-ylcarbamoyl)quinolines and pharmaceutically acceptable salts thereof are potent anti-allergic agents.

4 Claims, No Drawings

8-(1H-TETRAZOL-5-YL-CARBAMOYL)QUINOLINE COMPOUNDS

This is a continuation-in-part of application Ser. No. 766,511, filed Feb. 7, 1977, and now abandoned.

This invention relates to certain 8-(1H-tetrazol-5-ylcarbamoyl)quinolines, to pharmaceutically acceptable salts thereof, and to the use of these compounds as anti-allergic agents.

BACKGROUND OF THE INVENTION 2-(1H-Tetrazol-5-ylcarbamoyl)quinolines are known (German Offenlegungschrift No. 2,332,731; Chemical Abstracts 146174h, 1975) but have much lower potency and safety as anti-allergic agents than do the compounds of the present invention.

DETAILED DESCRIPTION OF THE INVENTION

This invention relates to physiologically active compounds which can be represented by the formula

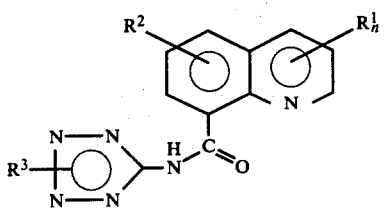

wherein $R^1$ is alkyl or alkoxy of one or two carbon atoms, $R^2$ is alkyl or alkoxy of one or two carbon atoms, hydrogen, nitro or halogen, $R^3$ is hydrogen or alkyl of one to four carbon atoms and n is zero, one or two, and pharmaceutically acceptable salts thereof (including alkali metal salts, e.g. sodium, and organic base salts, e.g. dimethylaminoethanol). R' in the foregoing formula is bonded to a carbon atom of the ring.

In the foregoing formula, the circle in the tetrazole ring signifies a pair of double bonds which, together with the bonds shown, satisfy all of the valences of the ring carbon atom and all but one valence of the four ring nitrogen atoms. That remaining nitrogen valence is satisfied by $R^3$.

In the compounds of the invention in which the tetrazole ring is unsubstituted, the hydrogen atom exists in tautomeric form on either the $N^1$ or the $N^2$ atom, i.e.

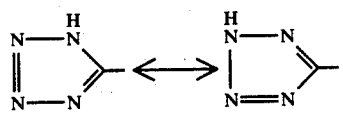

For convenience, however, this has been depicted herein simply as appearing on the $N^1$ atom. Such tautomerism does not occur in the compounds in which the tetrazole ring is substituted by an alkyl group (the substituent group remaining in a single location).

The invention also relates to anti-allergic compositions containing the compounds and to an anti-allergic method which comprises applying a compound of the invention to a mammalian organism in need thereof.

Presently preferred compounds of the invention are those wherein n is zero (i.e. the 2, 3 and 4 positions of the quinolino moiety are unsubstituted) and $R^2$ is hydrogen. Another preferred subclass is compounds wherein one of the nitrogens of the tetrazole ring is substituted by alkyl of one to four carbon atoms and most preferably by methyl. When an alkyl or alkoxy substituent is present anywhere in the compound, it preferably contains one carbon atom. The compounds of the invention wherein $R^2$ is chloro, iodo, methyl or nitro form a preferred subclass as do those compounds of the invention wherein $R^1$ is methyl.

The preferred compounds of the invention have oral activity and are as follows:
8-(1H-tetrazol-5-ylcarbamoyl)quinoline,
2-methyl-8-(1H-tetrazol-5-ylcarbamoyl)quinoline,
6-chloro-8-(1H-tetrazol-5-ylcarbamoyl)quinoline,
6-iodo-8-(1H-tetrazol-5-ylcarbamoyl)quinoline,
6-methyl-8-(1H-tetrazol-5-ylcarbamoyl)quinoline, and
8-(2-methyl-1H-tetrazol-5-ylcarbamoyl)quinoline The compounds of the present invention are readily prepared from known starting materials. The starting materials are aminotetrazole or alkyl aminotetrazole and various substituted 8-carboxyquinolines. Many substituted 8-carboxyquinolines and 8-carboxyquinoline itself are known, and the other substituted 8-carboxyquinolines are readily prepared by well-established methods of quinoline chemistry, e.g. from substituted anthranilic acids or substituted 2-cyanoanilines.

The substituted 8-carboxyquinoline starting materials of the present invention are converted to final product compounds of the invention by reaction with aminotetrazole. It is presently preferred to activate the 8-carboxy groups by techniques such as are used in peptide chemistry to convert a carboxylic acid group to an N-substituted carboxamide group. One preferred method for carboxyl activation is reaction of the carboxylic acid group with N,N'-carbonyl diimidazole. Other methods which may be used are reaction with thionyl chloride, reaction with N,N'-dicyclohexyl carbodiimide to provide the activated adduct, reaction with ethyl chloroformate, N-butyl chloroformate and the like to provide a mixed anhydride, reaction with p-nitrophenoxybenzyl chloride to provide a p-nitrophenoxybenzyl ester, and the like.

The activated 8-carboxyquinoline intermediate is then reacted with aminotetrazole in an aprotic solvent such as tetrahydrofuran or N,N-dimethylformamide, or in aqueous media in the presence of an acid acceptor, for example a tertiary organic base such as pyridine or triethylamine or an alkali metal carbonate or bicarbonate. Reactions in aqueous media may require a co-solvent in order to obtain reaction. Elevated temperatures may be used if necessary. Preferably the reaction temperatures are in the range of about 25°-200° C. The temperature used in a particular reaction will normally depend upon the solvent used, and will frequently be the reflux temperature of the mixture.

8-(N-Alkyl-1H-tetrazol-5-ylcarbamoyl)quinolines are readily prepared from known N-alkyltetrazoles or by alkylation of the tetrazole moiety of the corresponding unsubstituted compound of the invention with suitable alkylating agents such as alkyl bromides and iodides. Alkylation will generally result in a mixture of $N^1$ and $N^2$ substituted compounds. Separation is carried out by crystallization or chromatography.

The salts are prepared by reaction with the organic or inorganic base in a non-reactive solvent, e.g. with sodium hydroxide or dimethylaminomethanol.

The compounds of the invention have been shown to inhibit the release and/or synthesis and/or effect of biochemical products brought on in the mammalian organism by the combination of certain types of antibody and specific antigen. Both subjective and objective changes which result from the inhalation of specific antigen by sensitized subjects may be markedly inhibited by administration of the new compounds. The new compounds are useful in the treatment of so-called "intrinsic" asthma (in which no sensitivity to extrinsic antigen can be demonstrated) or any condition in which non-specific factors trigger the release of allergic mediators and in the treatment of other conditions in which antigen-antibody reactions are responsible for disease, for example extrinsic asthma, food allergies, allergic rhinitis, allergic conjunctivitis, atopic dermititis, hay fever, urticaria and anto-immune diseases.

The compositions of the invention normally comprise a compound of the invention in association with a pharmaceutically acceptable carrier or diluent. The nature of the composition and the carrier or diluent will, of course, depend upon the desired mode of administration, which may be, for example, orally by inhalation (orally or nasally), parenterally (as by intradermal or intravenous injection) or by topical application. They may be formulated in the conventional manner with conventional ingredients, e.g. they may be put up as solutions, suspensions, syrups, dry powders, tablets or, when intended for topical application, as creams, lotions or pastes. The compositions of the invention generally comprise a minor proportion of the active compound and a major proportion of carrier or diluent.

The compositions are preferably administered by inhalation, notably in the treatment of allergic asthma. For such use, the compounds of the invention, optionally in the form of a salt such as the sodium salt, are dissolved or suspended in water and may be applied by means of a conventional nebulizer. However, the administration of medicaments by means of a pressurized dispensing container, i.e. an aerosol dispenser, is an alternative to nebulizer administration. Aqueous solutions for administration by means of a conventional nebulizer may contain up to about 10 percent by weight of the active ingredient in sterile water; and compositions for dispensing from a pressurized container comprising suspensions or solutions in liquified propellants normally contain about 0.2 to 5 percent by weight of the active ingredient.

For administration from an aerosol dispenser, the medicament is dissolved or suspended in a liquified propellant medium. Suitable propellants are those conveniently used in formulations for dispensing from pressurized containers, for example, of the halogenated hydrocarbon-type such as fluoro- or fluorohalo-hydrocarbons and mixtures of any of these together with other propellants. Thus, see U.S. Pat. No. 2,868,691. Preferred propellants of low toxicity are difluorodichloromethane, dichlorotetrafluoroethane and mixtures thereof. Where the medicament is not soluble in the propellant, it may be necessary to add a surface-active agent to the composition in order to suspend the medicament in the propellant medium, and such surface-active agents may be any of those commonly used for this purpose, such as non-ionic surface-active agents. The use of such surface-active agents and the advantages which stem therefrom are more fully described in British Patent Specification No. 1,063,512.

When put up as powders, the compositions of the invention may be administered by means of a conventional insufflator device. In order to improve the properties of the powder for this purpose it is useful to modify the surface characteristics of the powder particles, for example, by coating them with a pharmaceutically acceptable material such as sodium stearate. In addition, finely divided powders of the active ingredients may be mixed with a coarser diluent material, such as lactose, which may be present in a smaller, equal or greater amount than the active ingredients, for example in from 50 to 150 percent by weight based on the weight of the active compound of the invention and such other active ingredients as may be present.

The compounds of the invention may also be administered by dispensers from which metered amounts of the compounds are discharged in a state to be orally or nasally received during inhalation, wherein the propellant is compressed air or other compressed inert gas such as nitrogen, argon and the like.

As noted previously, the compounds of the invention are indicated for use in inhibiting the effects of antibody-antigen reactions. The treatment may be one whch requires repeated dosages of the medicament at regular intervals. The amount of medicament and frequency of administration will depend upon many factors, and no concise dosage rate or regimen can be generally stated. However, as a general guide, where the compounds are administered by inhalation to a patient suffering from acute allergic asthma, therapeutically useful results may be achieved when doses of 0.1 to 20 mg/kg are used. When the compounds are administered by oral routes, larger dosages are normally given. The invention thus provides a method for inhibiting the effects of an antibody-antigen reaction which comprises the prior (preferably) or subsequent application to the known or expected area of the antibody-antigen reaction mechanism of a therapeutically effective amount of a compound of the invention.

The compounds of the invention may also find use in the treatment of allergic eye conditions, for example that associated with hay fever, i.e. allergic conjunctivitis. For such use they may be used in the form of eye drops and/or spray as an isotonic aqueous solution containing about two percent of the compound and a preservative.

Other active ingredients may also be present in the compositions of the invention. Thus, in compositions for administration by inhalation, it may be beneficial to include a bronchodilator such as isoprenaline, adrenaline, carbuterol, rimiterol, orciprenaline, isoetharine or derivatives thereof, particularly salts. The amount of bronchodilator used will vary over a broad range, depending, inter alia, upon the nature and activity of the bronchodilator and the compound of the present invention which is used. However, the use of a minor proportion (i.e. less than 50 percent by weight) of the bronchodilator together with from 0.1 to 10 percent by weight of the compound of the present invention is preferred. Such compositions constitute an additional aspect of the invention.

The effectiveness of the compounds of the invention is evaluated by inhibiting passive cutaneous anaphylaxis in a standard test method substantially as described in "Immunology", 16, 749 (1969). The variation of the method generally used is as follows: Sprague-Dawley rats (male or female) having a body weight of about 200 grams are injected intramuscularly with egg albumin and intraperitoneally with *Bordetella pertussis* vaccine. Ten to twelve days after this treatment the rats are exsanguinated via the abdominal aorta to recover the blood, which is allowed to clot overnight. The blood samples are centrifuged in order to remove the blood serum containing the antibody.

This antibody is used in the following way: Sprague-Dawley rats weighing from 50 to 120 grams are sensitized by intradermal injection of 0.1 ml. of antibody-containing serum into the mid-dorsal region. Sensitivity is allowed to develop for 24 hours, and the test compounds are administered (either by intraperitoneal injection or orally) at dose levels selected to provide a range of inhibition values (suitable screening doses are 50, 25, 10 or 5 mg/kg). Six rats are used for each concentration of the compound under test. At various times thereafter (e.g. five minutes), the rats are then injected intravenously with an antigen which comprises 1 ml. of a mixture of egg albumin (0.5 mg/ml), Evans Blue dye solution (10 mg/ml) and physiological saline. Six rats are also used as controls for each test, the control rats being injected with the antibody and the antigen in the same way as the test rats but receiving no test compounds.

Forty-five minutes after injection of the egg albumin the rats are killed and the skins removed and reversed. The intensity of the anaphylactic reaction is assessed by comparing the size (area determined approximately from the product of two diameters of the dyed area taken at right angles) of the characteristic blue weal produced by spread of the Evans Blue dye from the sensitization site. The more intense the anaphylactic reaction, the larger is the area of the blue weal. Percent inhibitions are calculated using the formula $$\frac{(\text{Control Group Area} - \text{Treated Group Area}) \times 100}{\text{Control Group Area}}$$

and these values are plotted graphically for each compound so that the dosage required to achieve a 50 percent inhibition of the anaphylactic reaction ($ID_{50}$) can be determined. The compounds of the present invention are active in this test at non-toxic doses.

The following examples are provided for the purpose of further illustrating the invention but are not intended to limit the scope thereof in any way.

EXAMPLE 1

A solution of 1.0 g (6 mmole) of 8-quinoline carboxylic acid and 0.98 g. (6 mmole) of N,N'-carbonyldiimidazole in 40 ml. of N,N-dimethylformamide is stirred at 100° C. for six hours. To this mixture is added 0.62 g. (6 mmole) of 5-aminotetrazole monohydrate in 10 ml. of N,N-dimethylformamide which has been dried over molecular sieves. After stirring for one hour at 100° C., the solution is evaporated under vacuum. The residue is diluted with water and about 3 ml. of ten percent hydrochloric acid and stirred for one hour. The solid product is separated by filtration, dried and recrystallized from N,N-dimethylformamide. The white solid product is 8-(1H-tetrazol-5-ylcarbamoyl)quinoline, m.p. 310°–315° C. (dec.).

| Analysis: | % C | % H | % N |
|---|---|---|---|
| Calculated for $C_{11}H_8N_6O$: | 55.0, | 3.4, | 35.0 |
| Found: | 54.7, | 3.3, | 34.9. |

Using the method of Example 12 the following compounds of the invention are prepared from the starting quinolines listed in the table.

TABLE I

| Example No. | Starting Material | Product |
|---|---|---|
| 2 | 8-quinolinecarboxylic acid, 5-Cl | 5-Cl-8-(1H-tetrazol-5-ylcarbamoyl)quinoline, m.p. 305° C. |
| 3 | 8-quinolinecarboxylic acid, 5-I | 5-I-8-(1H-tetrazol-5-ylcarbamoyl)quinoline, m.p. 295°–297° C. |
| 4 | 8-quinolinecarboxylic acid, 5-CH$_3$ | 5-CH$_3$-8-(1H-tetrazol-5-ylcarbamoyl)quinoline, m.p. 296–297° C. |

TABLE I-continued

| Example No. | Starting Material | Product |
|---|---|---|
| 5 | 5-methoxy-8-quinolinecarboxylic acid (CH₃O-quinoline-HOOC) | corresponding 2H-tetrazol-5-yl carbamoyl product, m.p. 276–279° C. |
| 6 | 5-nitro-8-quinolinecarboxylic acid (O₂N-quinoline-HOOC) | corresponding product, m.p. 307–309° C. |
| 7 | 2-methyl-8-quinolinecarboxylic acid (quinoline-CH₃, HOOC) | corresponding product, m.p. 303–307° C. |
| 8 | 4-methyl-8-quinolinecarboxylic acid (CH₃-quinoline, HOOC) | corresponding product, m.p. > 290° C. |
| 9 | 6-methyl-8-quinolinecarboxylic acid (H₃C-quinoline, HOOC) | corresponding product, m.p. 287–289° C. |
| 10 | 6-chloro-8-quinolinecarboxylic acid (Cl-quinoline, HOOC) | corresponding product, m.p. 300°–301° C. |

EXAMPLE 11

To a solution of 1.7 g. (10 mmole) of 8-quinoline carboxylic acid in 50 ml. of N,N-dimethylformamide is added 1.6 g. (10 mmole) of carbonyl diimidazole, and the mixture is stirred for four hours at 100° C.

The reactive intermediate which is formed is reacted with 1.0 g. (10 mmole) of 5-amino-2-methyltetrazole. The reaction is carried out by adding the solution and two drops of trifluoroacetic acid to the stirred solution of reactive intermediate and heating for four hours at 140°–150° C. The solution is then evaporated to remove the N,N-dimethylformamide. Water is added to the residue, the mixture is cooled, then filtered. The solid product is recrystallized from ethanol to provide 8-(2-methyl-1H-tetrazol-5-ylcarbamoyl)quinoline, m.p. 222°–223° C.

| Analysis: | % C | %H | %N |
|---|---|---|---|
| Calculated for $C_{12}H_{10}N_6O$: | 56.7; | 4.0; | 33.0 |
| Found: | 56.7; | 4.1; | 33.1. |

EXAMPLE 12

A mixture of 2.4 g. (0.020 mole) of 8-quinolinecarboxylic acid and 3.0 g. (0.030 mole) of 5-amino-1-methyltetrazole is stirred in 30 ml. of pyridine at 20° C. while adding 2.0 ml. of thionyl chloride dropwise. The mixture is heated at 70° C. for one hour. The reaction mixture is evaporated to provide a residue which is diluted with water. The solid is separated by filtration and recrystallized from acetic acid with decolorizing charcoal. The product is recrystallized a second time from acetic acid to provide 8-(1-methyl-1H-tetrazole-5-yl-carbamoyl)quinoline, m.p. 224°–225° C.

| Analysis: | % C | % H | % N |
|---|---|---|---|
| Calculated for $C_{12}H_{10}N_6O$: | 56.7; | 4.0; | 33.1 |
| Found: | 56.4; | 4.0; | 32.7 |

EXAMPLE 13

To a solution of 4.7 g. (0.026 mole) of 7-methyl-8-quinolinecarboxylic acid, 3.9 g. (0.037 mole) of 5-aminotetrazole hydrate in 30 ml. of pyridine and 50 ml. of chloroform is added dropwise with stirring 5.6 ml. of thionyl chloride. The mixture is stirred at 70° C. for about one hour. The reaction mixture is evaporated to provide a residue which is diluted with water. The precipitate is separated by filtration and recrystallized from acetic acid. The product is again recrystallized from ethanol to provide 7-methyl-8-(1H-tetrazole-5-ylcarbamoyl)quinoline, m.p. 285°–287° C.

| Analysis: | % C | % H | % N |
|---|---|---|---|
| Calculated for $C_{12}H_{10}N_6O$: | 56.7; | 4.0; | 33.1 |
| Found: | 56.6; | 3.8; | 33.1. |

EXAMPLE 14

Using the method of Example 12, starting with 5-chloro-4-methyl-8-quinoline carboxylic acid, the product obtained is 5-chloro-4-methyl-8-(1H-tetrazole-5-ylcarbamoyl)quinoline, m.p. 300° C.

| Analysis: | % C | % H | % N |
|---|---|---|---|
| Calculated for $C_{12}H_9ClN_6O$: | 49.9; | 3.1; | 29.1 |
| Found: | 49.9; | 3.0; | 29.4. |

EXAMPLE 15

To a stirred ice bath-cooled solution of 4.0 g. (0.020 mole) of 2,4-dimethyl-8-quinoline carboxylic acid in 20 ml. of N,N-dimethyl formamide is added 2.8 ml. of triethyl amine. To this solution is added dropwise 2 ml. of ethylchloroformate. The mixture is stirred for one hour, then 2 g. (0.020 mole) of 2-aminotetrazole monohydrate in 10 ml. of N,N-dimethylformamide is added. The mixture is stirred at 20° C. for about 16 hours then evaporated to provide a residue which is washed with water. The residue is recrystallized twice from acetic acid to provide 2,4-dimethyl-8-(1H-tetrazole-5-ylcarbamoyl)quinoline, m.p. 300°–305° C.

EXAMPLE 16

Using the method of Example 12, starting with 5-methoxy-8-quinoline carboxylic acid, the product obtained is 5-methoxy-8-(1H-tetrazol-5-ylcarbamoyl)quinoline, m.p. 276°–279° C.

| Analysis: | % C | % H | % N |
|---|---|---|---|
| Calculated for $C_{11}H_{10}N_6O_2$: | 53.3; | 3.7; | 31.1 |
| Found: | 53.0; | 3.7; | 31.1. |

EXAMPLE 17

Using the method of Example 12, starting with 6-hydroxy-8-quinoline carboxylic acid, the product obtained is 6-hydroxy-8-(1H-tetrazol-5-ylcarbamoyl)quinoline, m.p. >320° C.

| Analysis: | % C | % H | % N |
|---|---|---|---|
| Calculated for $C_{11}H_8N_6O_2$: | 51.6; | 3.1; | 32.8 |
| Found: | 51.5; | 3.2; | 32.7. |

EXAMPLE 18

Using the method of Example 12 and starting with 1-(n-butyl)tetrazole, the product 8-(1-n-butyl-1H-tetrazol-5-yl-carbamoyl)quinoline is obtained.

EXAMPLE 19

Methyl 4-hydroxyquinoline-8-carboxylate is converted first to the corresponding 4-chloro ester (utilizing phosphorous oxychloride) then to the 4-methoxy ester (with sodium methoxide). This compound, methyl 4-methoxyquinoline-8-carboxylate, is then hydrolyzed with sodium hydroxide to the free acid, 4-methoxyquinoline-8-carboxylic acid. Using the method of Example 1, the compound, 4-methoxy-8-(1H-tetrazol-5-ylcarbamoyl)quinoline, is prepared from this compound and 5-aminotetrazole monohydrate.

What is claimed is:

1. A compound of the formula

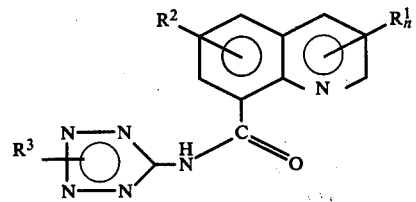

wherein $R^1$ is alkyl or alkoxy of one or two carbon atoms, $R^2$ is alkyl or alkoxy of one or two carbon atoms, hydrogen, nitro or halogen, $R^3$ is hydrogen or alkyl of one to four carbon atoms and n is zero, one or two, and pharmaceutically acceptable salts thereof.

2. The compound 8-(1H-tetrazol-5-ylcarbamoyl)quinoline according to claim 1.

3. The compound 6-iodo-8-(1H-tetrazol-5-ylcarbamoyl)quinoline according to claim 1.

4. The compound 8-(2-methyl-1H-tetrazol-5-ylcarbamoyl)quinoline according to claim 1.

* * * * *